United States Patent
Kumar et al.

(10) Patent No.: US 6,822,119 B1
(45) Date of Patent: Nov. 23, 2004

(54) PROCESS FOR THE PREPARATION OF TOLTERODINE

(75) Inventors: Yatendra Kumar, Haryana (IN); Mohan Prasad, Haryana (IN); Praveen Kumar Neela, Andhra Pradesh (IN); Satyananda Misra, Haryana (IN)

(73) Assignee: Ranbaxy Laboratories Limited, New Delhi (IN)

( * ) Notice: Subject to any disclaimer, the term of this patent is extended or adjusted under 35 U.S.C. 154(b) by 0 days.

(21) Appl. No.: 10/485,585

(22) PCT Filed: Aug. 2, 2002

(86) PCT No.: PCT/IB02/03012

§ 371 (c)(1),
(2), (4) Date: May 18, 2004

(87) PCT Pub. No.: WO03/014060

PCT Pub. Date: Feb. 20, 2003

(30) Foreign Application Priority Data

Aug. 3, 2001 (IN) ............................. 829/2001

(51) Int. Cl.$^7$ ............................. C09B 11/02
(52) U.S. Cl. ..................... 564/316; 564/315
(58) Field of Search .................. 564/316, 315

(56) References Cited

U.S. PATENT DOCUMENTS

| 5,382,600 A | 1/1995 | Jönsson et al. | ............. 514/603 |
| 5,922,914 A | 7/1999 | Gage et al. | ................. 564/413 |

*Primary Examiner*—Samuel Barts
(74) *Attorney, Agent, or Firm*—Jayadeep R. Deshmukh, Esq.; George E. Heibel, Esq.; William D. Hare, Esq.

(57) ABSTRACT

The present invention relates to a cost effective and industrially advantageous process for the preparation of tolterodine and pharmaceutically acceptable salts thereof.

11 Claims, No Drawings

PROCESS FOR THE PREPARATION OF TOLTERODINE

FIELD OF THE INVENTION

The present invention relates to a cost effective and industrially advantageous process for the preparation of tolterodine, and pharmaceutically acceptable salts thereof.

BACKGROUND OF THE INVENTION

Tolterodine is a muscarinic receptor antagonist which has recently been launched for the treatment of urinary urge incontinence and other symptoms of bladder overactivity. Chemically, tolterodine is (+)-(R)-3-(2-Hydroxy-5-methylphenyl)-N,N-diisopropyl-3-phenyl propylamine having structural formula I and was first disclosed in U.S. Pat. No. 5,382,600.

FORMULA I

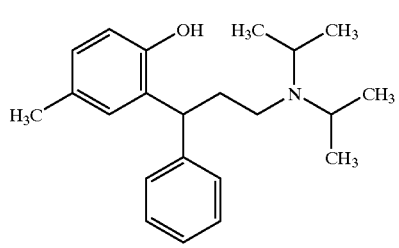

A process for preparing tolterodine is described in U.S. Pat. No. 5,382,600. The process involves the reaction of 3,4-dihydro-6-methyl-4-phenyl-2H-benzopyran-2-one of structural Formula II

FORMULA II

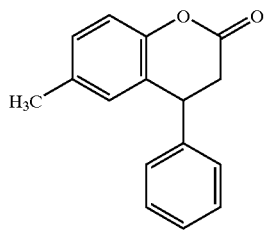

with methyl iodide and potassium carbonate in refluxing acetone/methanol to give methyl-3-(2-methoxy-5-methylphenyl) 3-phenyl propionate of Formula III.

FORMULA III

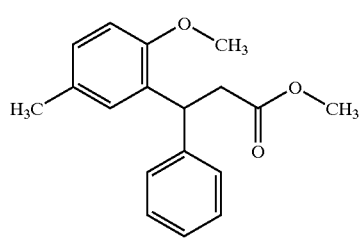

The ester of Formula III is reduced with lithium aluminium hydride in ether to the corresponding propanol of Formula IV

FORMULA IV

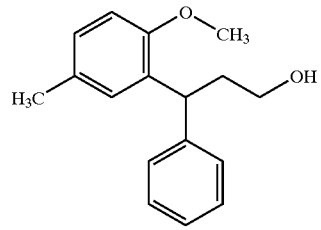

which is reacted with tosyl chloride and pyridine to yield the tosylate of Formula V

FORMULA V

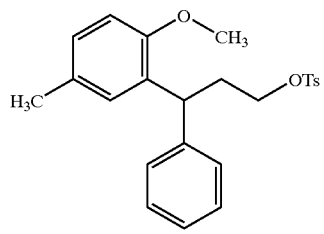

which on condensation with diisopropylamine in hot acetonitrile is converted into the tertiary amine of Formula VI.

FORMULA VI

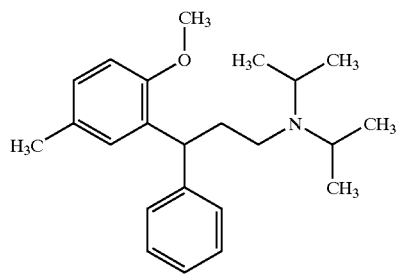

The compound of Formula VI is treated with boron tribromide in dichloromethane to give the amine of Formula I as a racemic mixture, which is resolved with L-(+) tartaric acid. Long reaction time and low overall yields makes this process very expensive and less productive. Furthermore, the use of expensive and hazardous reagents like methyl iodide, lithium aluminum hydride, and boron tribromide also renders this process unsuitable and hazardous on a commercial scale.

U.S. Pat. No. 5,922,914 provides an alternate method for the preparation of tolterodine. The process involves the cyclization of trans-cinnamic acid of Formula VIII

FORMULA VIII

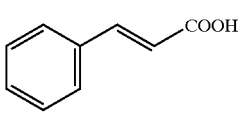

with p-cresol of Formula IX

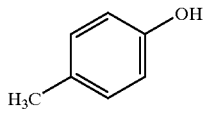
FORMULA IX in hot sulfuric acid to give 3,4-dihydro-6-methyl-4-phenyl-2H-benzopyran-2-one of Formula II which is reduced with diisobutyl aluminium hydride (DIBAL) in toluene to yield 6-methyl-4-phenyl-3,4-dihydro-2H-1-benzopyran-2-ol of Formula X

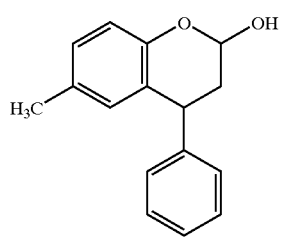
FORMULA X

The reductocondensation of compound of Formula X with diisopropylamine by means of hydrogen over palladium on charcoal in methanol affords racemic tolterodine of Formula I which is resolved with L-tartaric acid. This process is also not commercially feasible since it makes use of an expensive and hazardous reagent DIBAL. Although the number of steps are reduced but the cost incurred to produce tolterodine is high.

It is, therefore, desirable to solve the problems associated with the prior art and to provide an efficient process for the preparation of tolterodine which process improves the economics by employing less expensive and less hazardous raw materials and is more productive. The process is convenient to operate on a commercial scale and gives the desired product in good yield and quality.

SUMMARY OF THE INVENTION

The present invention provides a process for the preparation of tolterodine of structural Formula I, and pharmaceutically acceptable salts thereof,

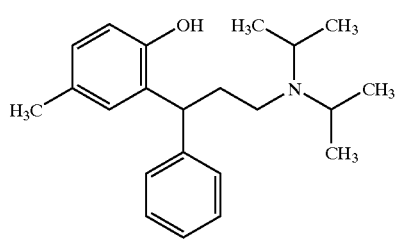
FORMULA I comprising:

(a) reacting 3,4-dihydro-6-methyl-4-phenyl-2H-benzopyran-2-one of structural Formula II

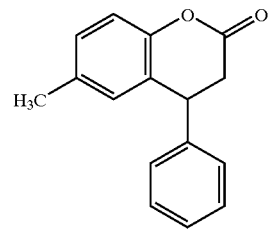
FORMULA II with dimethyl sulphate in the presence of sodium hydroxide, and a phase transfer catalyst to obtain methyl-3-(2-methoxy-5-methylphenyl)-3-phenyl propionate of Formula III,

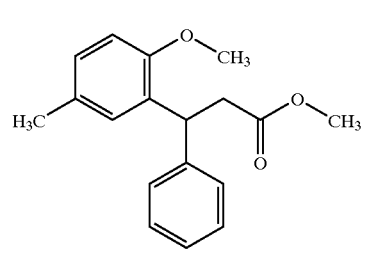
FORMULA III (b) reducing the ester of Formula III with a reducing agent in the presence of a Lewis acid to obtain 3-(2-methoxy-5-methylphenyl)-3-phenyl propanol of Formula IV,

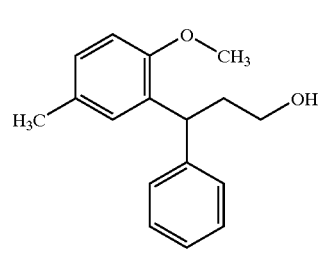
FORMULA IV (c) protecting the hydroxy group of the alochol of Formula IV to give a compound of Formula V,

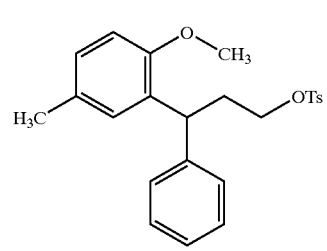
FORMULA V (d) aminating with diisopropylamine to give N,N-diisopropylamine-3-(2-methoxy-5-methylphenyl)-3-phenylpropylamine of Formula VI,

FORMULA VI

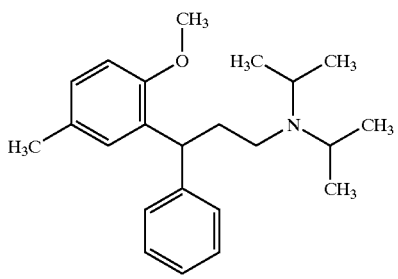

(e) removing the hydroxy protecting group to obtain N,N-diisopropyl-3-(2-hydroxy-5-methylphenyl)-3-phenylpropylamine of formula I and (f) if desired, converting the compound of formula I into its pharmaceutically acceptable salts.

The starting material, 3,4-dihydro-6-methyl-4-phenyl-2H-benzopyran-2-one of Formula II is prepared by methods known in the literature (Example 1 of U.S. Pat. No. 5,922,914).

The reaction at step a) is performed in the presence of a phase transfer catalyst to yield the compound of Formula III. The phase transfer catalyst used is selected from the group consisting of tetrabutylammonium bromide, tetrabutylammonium chloride, and tetrabutylammonium hydrogen sulphate.

The reducing agent used at step b) is a metal hydride such as sodium borohydride in the presence of a Lewis acid. The Lewis acid used is selected from the group consisting of boron trifluoride, aluminium chloride, ferric chloride and zinc bromide. The solution of the ester of Formula III in an organic solvent is treated with sodium borohydride in combination with aluminium chloride at about 25–30° C. for about 2–3 hours. After a suitable work up 3,3-diphenylpropanol of Formula IV is obtained. The organic solvent is selected from inert solvents such as acetone, dioxane, acetonitrile, chloroform, benzene, methylene chloride, tetrahydrofuran, ethyl acetate, N,N-dimethylformamide, pyridine, monoglyme, diglymne, and mixtures thereof.

The protecting group used in step c) is an arylsulfonyloxy group such as p-toluene sulphonyl chloride. The reaction of step c) is performed in methylene chloride at about 10–25° C. for 4–5 hours in the presence of triethylamine. After a suitable work up, the protected intermediate compound of Formula V is obtained.

The amination of compound of Formula V at step d) is carried out with diisopropylamine in an autoclave to give a compound of Formula VI. The removal of hydroxy protective groups can be achieved by treatment with hydrobromic acid, boron tribromide or by catalytic hydrogenation. It is preferably carried out with aqueous hydrobromic acid in acetic acid. The reaction of step e) is performed at about 70–115° C. to afford tolterodine hydrobromide.

Tolterodine is an amine and forms acid addition salts both with organic and inorganic acids. Examples of such salts include hydrochloride, hydrobromide, sulfate, methane sulfonate, phosphate, nitrate, benzoate, citrate, tartarate, fumarate and meleate.

DETAILED DESCRIPTION OF THE INVENTION

In the following section one preferred embodiment is described by way of example to illustrate the process of this invention. However, it is not intended in any way to limit the scope of the present invention.

EXAMPLE

Step a)—Preparation of methyl-3-(2-methoxy-5-methylphenyl)-3-phenyl propionate (III)

3,4-dihydro-6-methyl-4-phenyl-2H-benzopyran-2-one (250 g, 1.05 mol) of Formula II in aqueous sodium hydroxide solution (134.3 g in 1 L water) was heated to 70–80° C. The solution was cooled to 25–30° C. and methylene chloride and tetrabutylammonium bromide (TBAB) was added. It was followed by the slow addition of dimethyl sulfate and the reaction mixture was further stirred for 2–4 hours. The organic layer was separated, dried and evaporated to give the titled compound as viscous oil (301 g); Purity (by HPLC) >99%.

Step b): Preparation of 3-(2-methoxy-5-methylphenyl)-3-phenylpropanol (IV).

The ester of formula III (295 g, 1.04 mol) was dissolved in 500 ml monoglyme and sodium borohydride (45.4 g, 1.19 mol) was added at room temperature. The mixture was cooled to 0° C. and anhydrous aluminium chloride was added slowly. The reaction mixture was stirred for 2–3 hours at 25–30° C. and then decomposed by the addition of dilute hydrochloric acid. Monoglyme was distilled under reduced pressure and the reaction mixture was filtered to remove the salts. The aqueous layer was extracted with methylene chloride and evaporated under reduced pressure to give the titled product as an oil (265 g); Purity (by HPLC)>99%.

Step c)—Preparation of 3-(2-methoxy-5-methylphenyl)-3-phenylpropyl-p-toluene sulphonate (V)

The propanol of Formula IV (260 g, 1.02 mol) was dissolved in methylene chloride. The solution was cooled to 0° C. and triethylamine (158.3 g, 1.56 mol) and p-toluene sulfonyl chloride (228, 1.19 mol) was added at 0° C. all at once. The reaction mixture was stirred for 4–5 hours at 10–20° C. It was cooled to 0° C. and water and concentrated hydrochloric acid were added. The organic layer was separated and washed with water. The solvent was removed under reduced pressure and diisopropyl ether was added. It was cooled to 0° C. and stirred for 3–4 hours. The product so separated was filtered, washed with diisopropyl ether and dried under reduced pressure to give the titled product (358 g) in 86% yield; Purity (by HPLC)>98.78%.

Step d)—Preparation of N,N-diisopropyl-3-(2-methoxy-5-methylphenyl)3-phenylpropyl amine (VI).

The tosylate of Formula V (355 g, 0.865 mol) was heated with acetonitrile and diisopropyl amine (1:1) at 80° C. in a pressure bottle (autoclave) for 50–55 hours. The solvent was removed under vacuum and the residue was basified with sodium hydroxide and extracted with methylene chloride. The extract was washed with water, the solvent was removed under vacuum and the residue was dissolved in dilute hydrochloric acid. The solution was washed with diisopropyl ether, basified and extracted with methylene chloride. The extract was washed with water, dried and evaporated to give the titled product as an oil (228.65 g).

Step e)—Preparation of N,N-diisopropyl-3-(2-hydroxy-5-methylphenyl)-3-phenylpropyl amine hydrobromide (tolterodine hydrobromide) (1).

The amine of Formula VI (225 g, 0.663 mol) was heated with aqueous hydrobromic acid (500 ml) and acetic acid (300 ml) to reflux temperature (110–115° C.) for 10–12 hours. The reaction mixture was cooled to room temperature, maintained for 1 hour at room temperature and then filtered. The product so obtained was washed with water and dried under vacuum to yield the titled product. (234 g) in 86% yield; Purity (by HPLC) 97.5%.

While the present invention has been described in terms of its specific embodiments, certain modifications and equivalents will be apparent to those skilled in the art and are intended to be included within the scope of the present invention.

We claim:

1. A process for the preparation of tolterodine of structural Formula I, and pharmaceutically acceptable salts thereof,

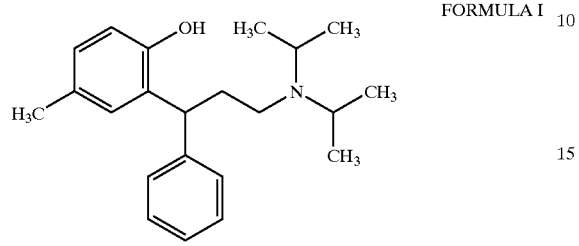

FORMULA I comprising:
(a) reacting 3,4-dihydro-6-methyl-4-phenyl-2H-benzopyran-2-one of structural Formula II

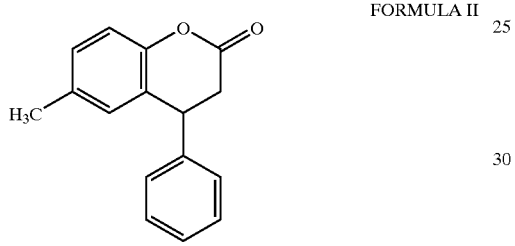

FORMULA II with dimethyl sulphate in the presence of sodium hydroxide, and a phase transfer catalyst to obtain methyl-3-(2-methoxy-5-methylphenyl)-3-phenyl propionate of Formula III,

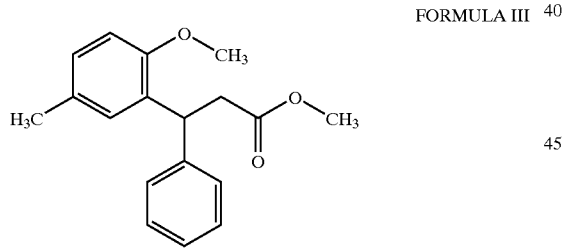

FORMULA III (b) reducing the ester of Formula III with a reducing agent in the presence of a Lewis acid to obtain 3-(2-methoxy-5-methylphenyl)-3-phenyl propanol of Formula IV,

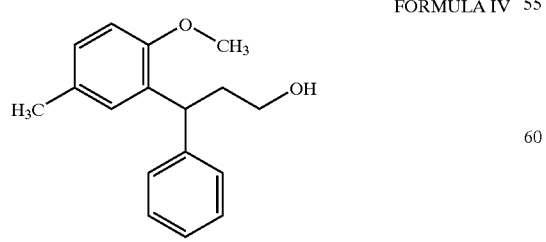

FORMULA IV (c) protecting the hydroxy group of the alcohol of Formula IV to give a compound of Formula V,

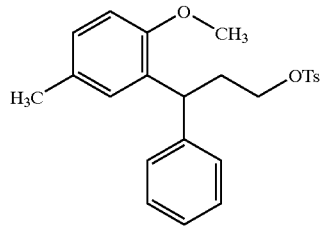

FORMULA V (d) aminating with diisopropylamine to give N,N-diisopropyl-3-(2-methoxy-5-methylphenyl)-3-phenylpropylamine of Formula VI, and

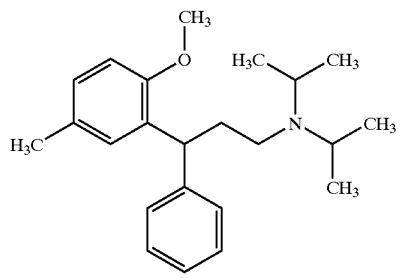

FORMULA VI (e) removing the hydroxy protecting group to obtain N,N-diisopropyl-3-(2-hydroxy-5-methylphenyl)-3-phenylpropylamine of Formula I.

2. The process according to claim 1 wherein the phase transfer catalyst used at step a) is selected from the group consisting of tetrabutylammonium bromide, tetrabutylammonium chloride and tetrabutylammonium hydrogen sulphate.

3. The process according to claim 2 wherein the phase transfer catalyst is tetrabutylammonium bromide.

4. The process according to claim 1, wherein the Lewis acid of step b) is selected from the group consisting of boron trifluoride, aluminium chloride, ferric chloride, and zinc bromide.

5. The process according to claim 4 wherein the Lewis acid is aluminium chloride.

6. The process according to claim 1 wherein the reducing agent used at step b) is sodium borohydride in combination with aluminium chloride.

7. The process according to claim 1, wherein during step b) the ester is reduced in the presence of an organic solvent.

8. The process according to claim 7 wherein the organic solvent is selected from the group consisting of acetone, dioxane, acetonitrile, chloroform, benzene, methylene chloride, tetrahydrofuran, ethyl acetate, N,N-dimethylformamide, pyridine, monoglyme, diglyme, and mixture(s) thereof.

9. The process according to claim 8 wherein the organic solvent is monoglyme.

10. The process according to claim 1 wherein the protecting group used in step c) is p-toluene sulphonyl chloride.

11. The process according to claim 1 wherein the hydroxy protective group in step e) is removed by aqueous hydrobromic acid in acetic acid.

* * * * *